(12) United States Patent
Pappas

(10) Patent No.: US 6,797,005 B2
(45) Date of Patent: *Sep. 28, 2004

(54) DEEP FLEXION POSTERIOR STABILIZED KNEE REPLACEMENT WITH BEARING TRANSLATION

(75) Inventor: Michael J. Pappas, Caldwell, NJ (US)

(73) Assignee: Biomedical Engineering Trust, South Orange, NJ (US)

(*) Notice: Subject to any disclaimer, the term of this patent is extended or adjusted under 35 U.S.C. 154(b) by 118 days.

This patent is subject to a terminal disclaimer.

(21) Appl. No.: 10/212,616

(22) Filed: Aug. 2, 2002

(65) Prior Publication Data

US 2003/0009229 A1 Jan. 9, 2003

Related U.S. Application Data

(63) Continuation-in-part of application No. 09/796,281, filed on Feb. 28, 2001, now Pat. No. 6,475,241.
(60) Provisional application No. 60/309,857, filed on Aug. 3, 2001.

(51) Int. Cl.$^7$ .................................................. A61F 2/38
(52) U.S. Cl. ................................ 623/20.27; 623/20.29
(58) Field of Search ........................... 623/20.27, 20.29, 623/20.15, 20.19, 20.21, 20.28, 20.33, 20.34

(56) References Cited

U.S. PATENT DOCUMENTS

| | | | |
|---|---|---|---|
| 4,298,992 A | * | 11/1981 | Burstein et al. ......... 623/20.27 |
| 4,309,778 A | | 1/1982 | Buechel et al. |
| 4,470,158 A | | 9/1984 | Pappas et al. |
| 4,568,348 A | | 2/1986 | Johnson et al. |
| 4,634,444 A | | 1/1987 | Noiles |
| 4,888,021 A | | 12/1989 | Forte et al. |
| 5,330,534 A | | 7/1994 | Herrington et al. |
| 5,395,401 A | * | 3/1995 | Bahler ..................... 623/20.29 |
| 5,489,311 A | | 2/1996 | Cipolletti |
| 5,658,342 A | | 8/1997 | Draganich et al. |
| 5,702,448 A | | 12/1997 | Buechel |
| 5,702,466 A | | 12/1997 | Pappas et al. |
| 5,824,100 A | * | 10/1998 | Kester et al. ............ 623/20.31 |
| 6,475,241 B2 | * | 11/2002 | Pappas .................... 623/20.29 |
| 2002/0156535 A1 | * | 10/2002 | Pappas .................... 623/20.29 |

* cited by examiner

*Primary Examiner*—Pedro Philogene
(74) *Attorney, Agent, or Firm*—Gerald E. Hespos; Anthony J. Casella

(57) ABSTRACT

A knee joint prosthesis includes femoral and tibial components, a bearing and a control arm. The bearing includes an inferior surface in sliding bearing engagement with the tibial component and a superior surface in articular bearing engagement with the femoral component. A notch extends into the posterior end of the bearing and a groove extends anteriorly from the notch in the inferior surface of the bearing. The posterior portions of the femoral component define a cam box having medial and lateral walls and a cam extending therebetween. The control arm is slidably engaged in the groove of the bearing and pivotally engage on the tibial component. The control arm further includes a post that extends into the cam box. The post includes a cam surface that engages the femoral cam to generate roll back of the femoral component on the bearing during flexion.

8 Claims, 12 Drawing Sheets

Fig. 23
Full Extension

Fig. 24
30° Flexion
Anterior Position

Fig. 25
30° Flexion
Posterior Position

Fig. 26
45° Flexion

Fig. 27
60° Flexion

Fig. 28
90° Flexion

Fig. 29
120° Flexion

Fig. 30
135° Maximum
Active Flexion

Fig. 31
162° Maximum
Passive Flexion

DEEP FLEXION POSTERIOR STABILIZED KNEE REPLACEMENT WITH BEARING TRANSLATION

This application claims priority on U.S. Provisional Patent Application No. 60/309,857, filed Aug. 3, 2001 and is a continuation-in-part of U.S. patent application Ser. No. 09/796,281, filed Feb. 28, 2001, now U.S. Pat. No. 6,475, 241.

BACKGROUND OF THE INVENTION

1. Field of the Invention

The subject invention relates to a knee joint prosthesis, and particularly a posterior stabilized replacement knee joint prosthesis.

2. Description of the Related Art

A natural knee joint includes the distal end of the femur with articular cartilage, the proximal end of the tibia with articular cartilage and a meniscus between the femur and tibia. The femur and the tibia are held in a proper relationship to the bearing by ligaments. These stabilizing ligaments include the posterior cruciate ligament, the anterior cruciate ligament and collateral ligaments.

Flexion of the knee causes the tibia to rotate relative to the femur about an axis that extends generally in a medial-to-lateral direction and simultaneously causes the contact area of the femur to roll back relative to the tibia. Flexion also generates rotation of the tibia about its own axis. The amount of rotation of the tibia during flexion of the knee is controlled and limited by the ligaments.

The natural knee joint can become damaged or diseased. For example, damage or disease to the knee can deteriorate the articular surfaces of the femur or tibia and can damage the articular cartilage between the bones. The prior art includes prosthetic knee joints to replace a damaged or diseased natural knee. A prosthetic knee joint typically includes a femoral component that is mounted to the distal end of a resected femur, a tibial component mounted to the proximal end of a resected tibia and a bearing between the femoral and tibial components. The inferior face of the femoral component of a prosthetic knee joint typically defines a pair of arcuate convex condyles. The superior face of the bearing has a corresponding pair of arcuately concave regions for articular bearing engagement with the condyles of the femoral component. The superior face of the tibial component may be substantially planar and is disposed in engagement with the inferior face of the bearing.

Prior art prosthetic knee joints have taken many different forms, depending upon the preferences of the orthopedic surgeon, the condition of the natural knee and the health, age and mobility of the patient. Some prior art knee joint prostheses fixedly secure the inferior surface of the bearing to the superior surface of the tibial component. Other prior art knee joint prostheses permit rotational movement between the bearing and the tibial component. Still other prior art knee joint prosthesis permit a controlled amount of anterior-posterior sliding movement between the bearing and a tibial component. Movement of the bearing relative to the tibial component achieves many functional advantages, as described in the prior art. Prior art knee joint prostheses that incorporate certain of the structural and functional features referred to above are disclosed in U.S. Pat. Nos. 4,470,158 and 4,309,778.

As noted above, the inferior bearing surface of the femoral component on most prosthetic knee joints comprises a pair of convexly arcuately condyles. The condyles of the femoral component are in articular bearing engagement with arcuately concave regions on the superior face of the bearing. Thus, the superior face of the bearing typically includes a pair of dished regions each of which has a relatively depressed center portion and a relatively elevated peripheral lip. As explained above, flexion of the knee joint causes the tibia to rotate about a medial-lateral axis relative to the femur. Flexion also causes the tibia to rotate around its own axis. These combined movements cause the condyles of the femur to ride up or climb the concavities on the superior surface of the bearing and to approach the peripheral lips of the bearing. Thus, flexion tends to move the relative components of the prosthetic knee toward dislocation. The degree to which dislocation is possible depends on several factors, most significantly, the presence or absence of ligaments. The likelihood of dislocation also depends upon the degree of flexion and on the degree of congruency between the inferior articular bearing surface of the femoral component and the superior surface of the bearing. For example, climbing of the femoral component on the bearing is not a significant problem in prosthetic knees that have a substantially flat superior surface on the bearing. However, the relatively great incongruency between the inferior bearing surface of the femoral component and the superior surface of the bearing on these prosthetic knees results in a very high contact stress that can damage the bearing. Prosthetic knees that have greater congruency between the femoral component and the bearing provide desirably low contact stress. However, the greater congruency when combined with a bearing that is slidable on the tibial component creates the problem of the tibial component climbing on the bearing, and hence creates the potential of dislocation. Climbing of the femoral component on the bearing also is a particular problem for prosthetic knee joints that employ a posterior stabilization post. In particular, the climbing of the femoral component on the bearing substantially increases sheer forces on the post and can lead to traumatic failure of the prosthesis.

Figure 18:
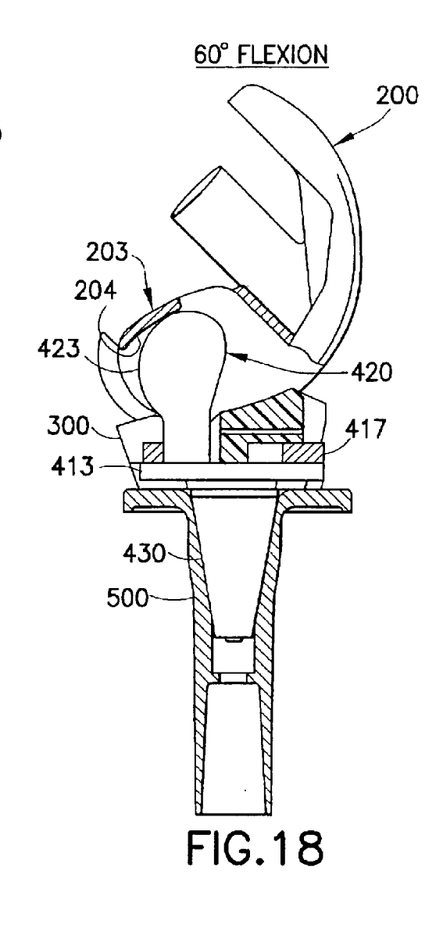
FIG. 18 is a cross-sectional view similar to FIGS. 16 and 17, but showing approximately 60° flexion.
Figure 19:
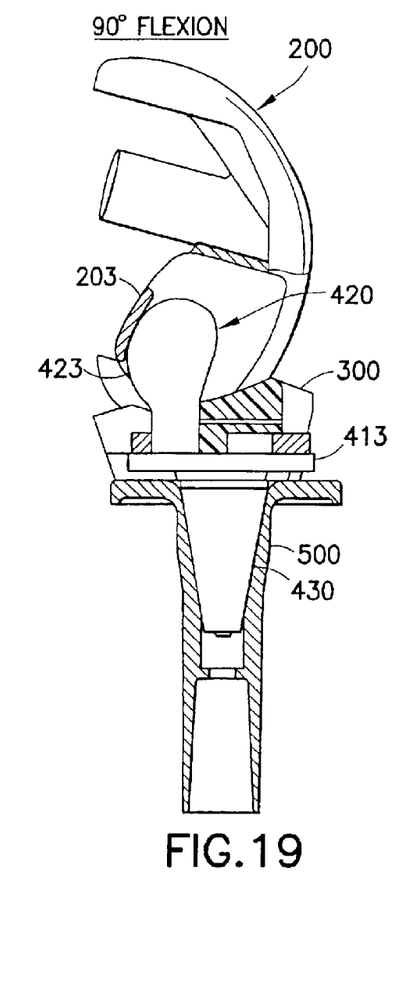
FIG. 19 is a cross-sectional view similar to FIGS. 16–18, but showing approximately 90° flexion.
Figure 20:
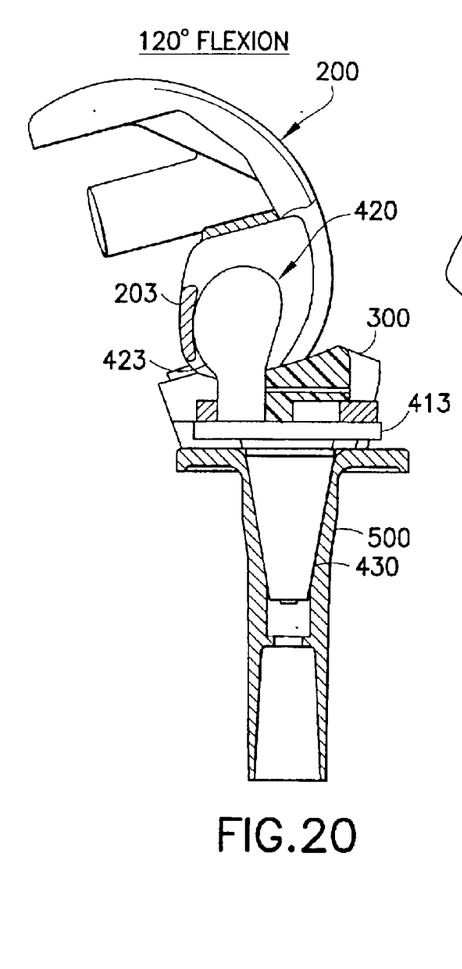
FIG. 20 is a cross-sectional view similar to FIGS. 16–19, but showing approximately 120° flexion.

Valgus-varus stability of a knee joint refers to the ability of the joint to resist the lateral forces or rotary forces that would cause rotation of the tibia relative to the femur in the frontal plane. Lateral forces or rotary movements that cause rotation of the tibia relative to the femur in the frontal plane tend to create a dislocation. Such dislocation is particularly likely to occur on either the medial or lateral side of the prosthesis, depending upon the direction of the lateral forces. Such a dislocation in a prior art prosthesis is shown in FIG. 18 hereto.

The prosthetic knee joint is under a compressive loading during normal activities. As a result, valgus-varus moments typically are resisted adequately by the articulating surfaces of the prosthetic components and by the ligaments. However, there are instances where additional valgus-varus stability may be desired, such as those instances where ligaments are deficient.

Some prior art prosthetic knee joints enhance valgus-varus stability by providing a stabilization post that extends into a posterior region between the femoral condyles. This region would be occupied by the posterior cruciate ligament if that ligament were present. Prosthetic knee joints that permit anterior-posterior sliding movement of the bearing on the tibial component provide superior roll back. In this regard, the term "roll back" refers to a posterior movement of the contact point of the femur relative to the tibia during flexion. Roll back, however, causes the femoral component to climb on the bearing, and thus increases the probability of dislocation. Additionally, this greater roll back and increases of climbing of the femoral component on the bearing substantially reduce shear forces on the posterior stabilizing post for those prosthetic joints that have such a posterior stabilizing post. A prosthetic bearing that can slide posteriorly during flexion avoids impingement between the bearing and anterior soft tissue of the knee. Thus, a prosthetic knee joint with a bearing capable of anterior-posterior sliding movement can avoid discomfort during deep flexion.

A prior art prosthetic knee joint with a stabilizing post and a bearing capable of anterior-posterior sliding movement is shown in U.S. Pat. No. 5,395,401 which issued to Bahler. In particular, U.S. Pat. No. 5,395,401 shows a prosthetic knee having a tibial component and a bearing slidably disposed on the superior face of the tibial component. The inferior surface of the bearing is provided with a dovetailed groove that extends along an anterior-posterior direction and at a location between the two concave condyles formed on the superior surface of the bearing. The bearing shown in U.S. Pat. No. 5,395,401 also includes a notch extending into the posterior portion of the bearing at a location between the two concave condyles of the bearing. The notch registers with the dovetailed groove of the bearing. The prosthesis of U.S. Pat. No. 5,395,401 further includes a control arm with a post that is pivotally engaged in a recess formed on the tibial component. The control arm includes a dovetailed portion that slidably engages in the dovetailed groove on the inferior surface of the bearing. The control arm shown in U.S. Pat. No. 5,395,401 also has a post that extends through the notch in the bearing and between the condyles of the femoral component. The post is dimensioned to slidably engage surfaces of the femoral component between the two convex condyles of the femoral component. However, nothing in U.S. Pat. No. 5,395,401 would prevent dislocation of the femur from the bearing.

Posterior stabilized design concepts developed for fixed bearings are not well adapted to mobile bearing knees. The recessing of the femoral patellar track, common in conventional posterior stabilized devices, is inconsistent with the use of a mobile patellar bearing and has also caused problems with fixed bearing designs. Climb, although a major problem with conforming tibial bearing surfaces, is not usually of great significance with the less conforming fixed bearing articulations.

The normal knee produces about 13 mm of rollback with 10 mm occurring in the first 30° of flexion. Typical current posterior stabilized devices fail to produce any significant rollback until about 70° of flexion. Thus rollback is not present during stair climbing, which is the most important activity where rollback is needed.

Failure to provide rollback where it is probably the most useful is clearly an undesirable characteristic. Further the highly incongruent cam contact of current posterior stabilized designs appears to be excessive even for limited activities such as arising from a seated position since even one such act can produce permanent deformation of the surface of the plastic cam.

The embodiment described here avoids excessive cam contact, as well as articulating contact, incongruity. It provides much more normal rollback characteristics than earlier posterior stabilized devices. Thus it appears to be a significant advance over these earlier designs.

SUMMARY OF THE INVENTION

The subject invention is directed to a knee joint prosthesis with an ability to resist dislocation at high degrees of flexion, but without dislocation resistance at low flexion. The knee joint prosthesis of the subject invention also provides resistance to valgus-varus moments.

The prosthesis of the subject invention includes a tibial component, a femoral component, a bearing and a control arm assembly. The tibial component includes an inferior projection configured for secure mounting in a recess formed in a resected tibia. The tibial component further includes a superior bearing surface having a conical recess extending therein and disposed within portions of the tibial component that define inferior mounting projection.

The femoral component includes a superior surface with a projection for mounting in a recess formed in a resected distal end of a femur. The femoral component further includes an inferior surface defining a pair of convex articular condyles. A notch extends into the posterior end of the femoral component and defines a cam box. The cam box has a pair of substantially parallel spaced apart medial and lateral sidewalls and a femoral cam that extends between superior locations on the sidewalls of the cam box.

The bearing includes a superior surface having a pair of concave arcuate bearing surfaces in articular bearing engagement with the condyles of the femoral component. The bearing further includes an inferior surface disposed in sliding bearing engagement with the superior surface of the tibial component. A dovetail groove is formed in the inferior surface of the bearing, and extends generally in an anterior-posterior direction. The bearing further include a notch extending into the posterior side of the bearing and continuously between the superior and inferior surfaces thereof. The notch is substantially centrally disposed between the medial and lateral extremes of the bearing and registers with the dovetail groove. The anterior end of the notch may include an undercut or step that faces posteriorly and inferiorly. The undercut may engage a portion of the control arm at high degrees of flexion of the joint for resisting dislocation. However, at lower degrees of flexion, the undercut will play substantially no role in the normal operation of the joint. The inferior surface of the bearing may further include a stop recess near anterior portions of the dovetail groove. The stop recess may engage a stop pin on the control arm assembly to limit anterior movement of the bearing.

The control arm assembly includes a conical bearing dimensioned to pivotally engage in the conical recess formed in the tibial component. A dovetail guide extends substantially orthogonally from the superior large diameter end of the conical bearing of the control arm assembly. The dovetail guide is engageable in the dovetail groove formed in the inferior face of the bearing. The control arm further includes a post projecting in a superior direction from the posterior end of the control arm. The post is dimensioned to be received slidably in the notches in the posterior faces of the bearing and the femoral component. Portions of the post adjacent the control arm may define a control arm boss. The boss, if present, is configured to slide into the undercut at the anterior end of the notch in the bearing as the joint approaches maximum deflection. A stop pin may project in a superior direction from the anterior end of the dovetail guide for engagement in the stop recess of the bearing.

The prosthetic joint of the subject invention provides valgus-varus stability in two ways. Under loading conditions the normal compressive load will press the femoral condyles against the matching superior bearing surface of the bearing. The match is such that under compression any rotation of the femoral component occurs around an axis extending in an anterior-posterior direction. Rotation about such an axis produces impingement between the side surfaces of the post of the control arm and the sidewalls of the cam box. This contact produces a reaction force that resists any valgus-varus moment applied to the joint. During non-load bearing phases, where any valgus-varus moment is small, the post may be subject to small bending loads since joint compression will not exist under these conditions. However, the post can be made strong enough to resist such bending moments.

As flexion of the joint progresses, the box cam surface will engage the cam surface of the post. This engagement will commence at about 30°–35° flexion. Flexion beyond about 30°–35° will force the femoral component posteriorly. Compressive force on the bearing and its concave shape will cause the bearing to move with the femoral component. This posterior movement, or femoral rollback, improves quadricep effectiveness. Slightly beyond about 120° of flexion, it is desirable to prevent any additional posterior motion of the bearing. This can be accomplished by engagement between the post stop surface of the control arm and the recess stop surface defined by the undercut in the notch of the bearing.

DETAILED DESCRIPTION OF THE PREFERRED EMBODIMENT

Figure 1:
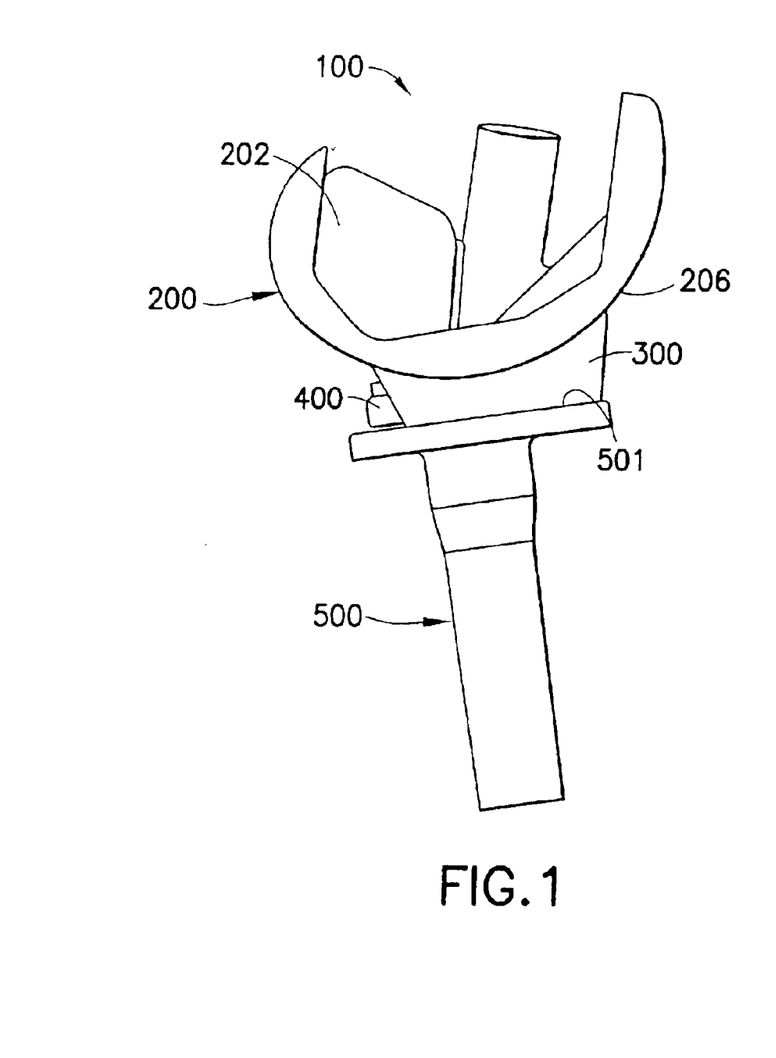
FIG. 1 is a side elevational view of a prosthetic joint in accordance with the subject invention.

The posterior stabilized knee replacement 100 consists of a femoral component 200, a bearing 300, a control arm assembly 400 and a tibial platform 500 as shown in FIG. 1.

Figure 2:
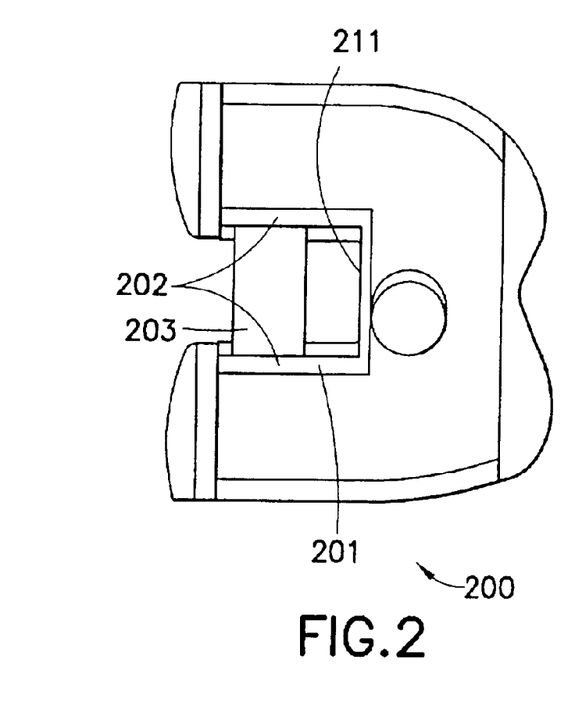
FIG. 2 is a top plan view of the femoral component of the prosthetic joint.
Figure 3:
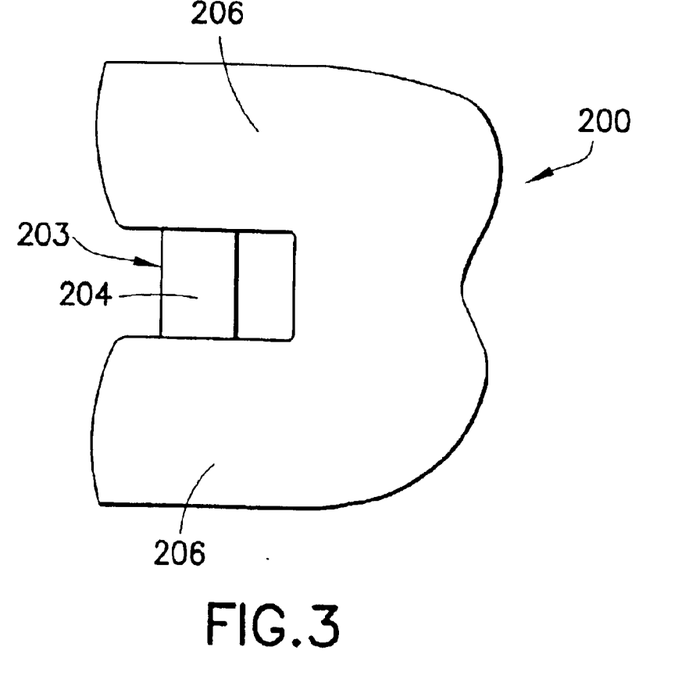
FIG. 3 is a bottom plan view of the femoral component.
Figure 16:
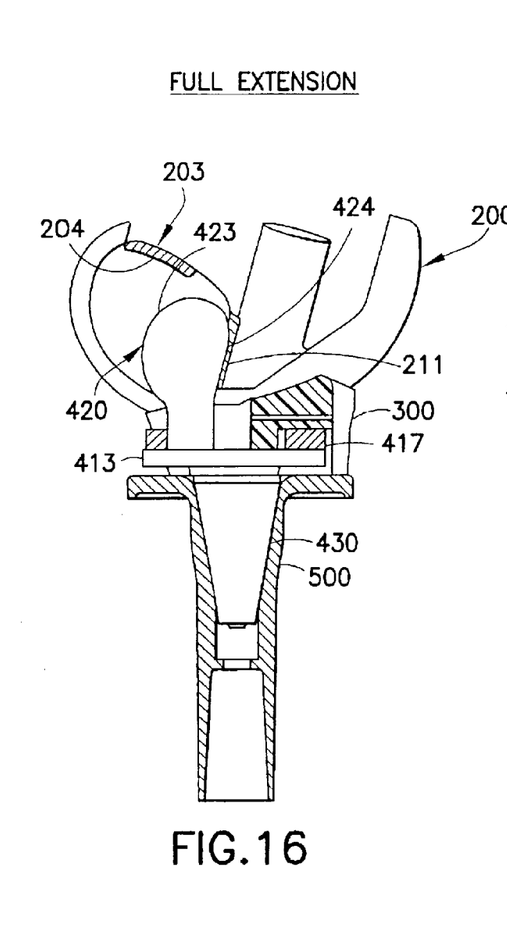
FIG. 16 is a cross-sectional view of the prosthetic joint at full extension.
Figure 17:
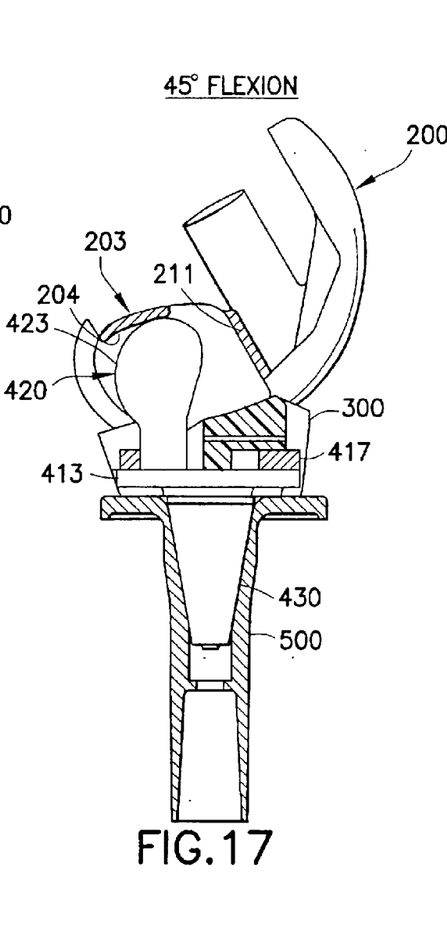
FIG. 17 is a cross-sectional view similar to FIG. 15, but showing approximately 45° flexion.

The femoral component 200, as shown in FIGS. 2 and 3, contains a cam box 201 with box sidewalls 202 and femoral cam 203. The femoral cam 203 includes a cam surface 204 that faces inferiorly at full extension, as shown in FIG. 16. In the embodiment of FIGS. 1–19, the femoral cam surface 204 is a single concave surface. In other embodiments, the cam surface could be a compound curve with convex surfaces separated by a concave surface. The cam box 201 also includes an anterior wall 211. The femoral component 200 is similar to that described in U.S. Pat. No. 5,702,466 except for the addition of the cam box 201 detail and a modular post for accepting an extensions to provide enhanced fixation. More particularly, the femoral component 200 includes a pair of convex condyles 206 that face inferiorly for articular bearing engagement with the bearing 300, as explained below.

Figure 4:
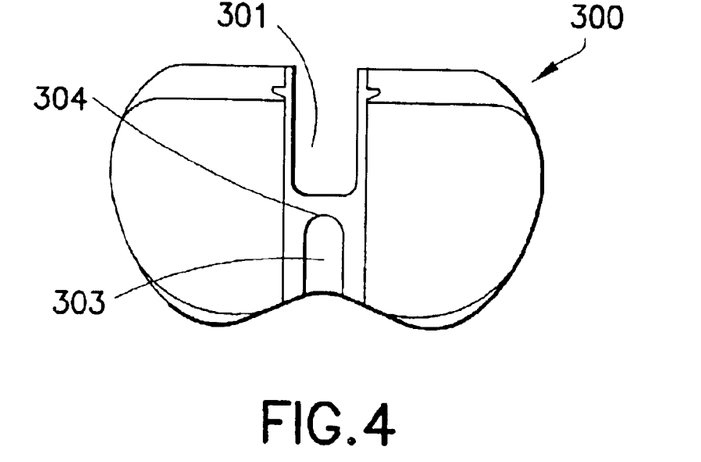
FIG. 4 is a bottom plan view of the bearing.
Figure 5:
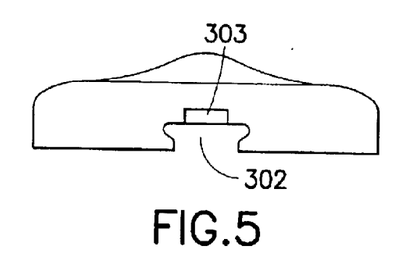
FIG. 5 is a front elevational view of the bearing.
Figure 6:
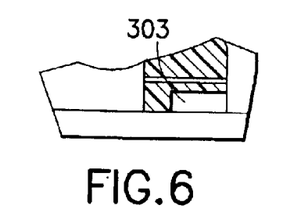
FIG. 6 is a cross-sectional view of the bearing.

The bearing 300, as shown in FIGS. 4–6, contains a posterior notch 301, a dovetail guide slot 302 and a stop recess 303 with a bearing stop surface 304.

Figure 7:
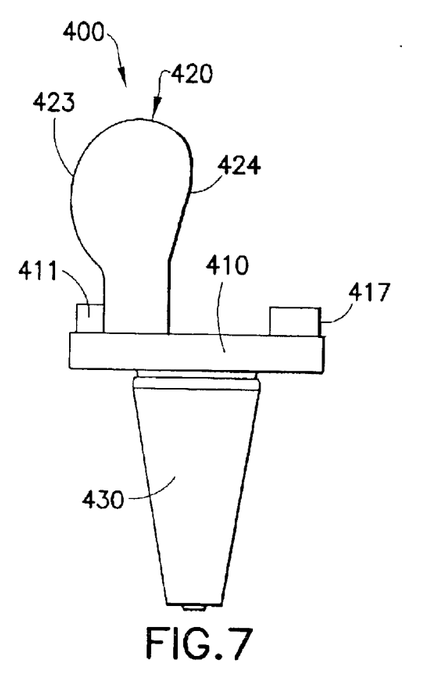
FIG. 7 is a side elevational view of the control arm.
Figure 8:
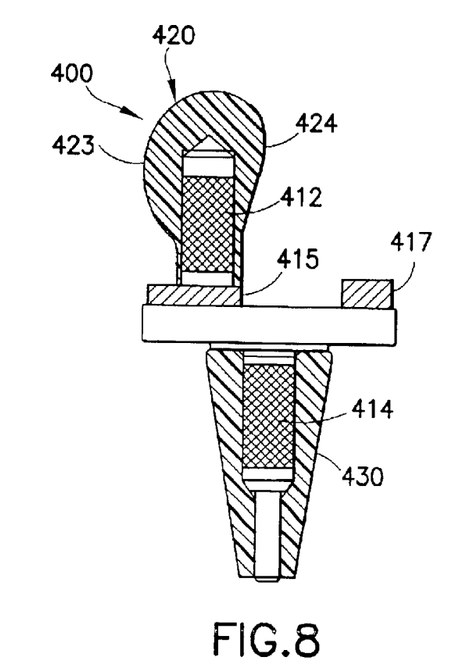
FIG. 8 is a cross-sectional view of the control arm.
Figure 9:
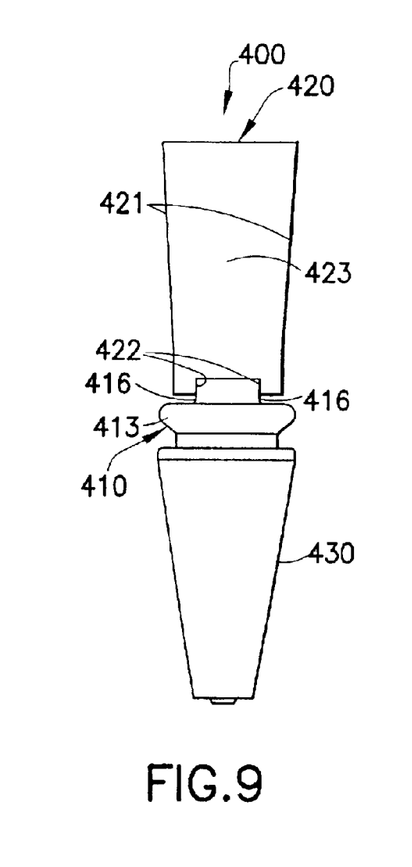
FIG. 9 is a rear elevational view of the control arm.
Figure 10:
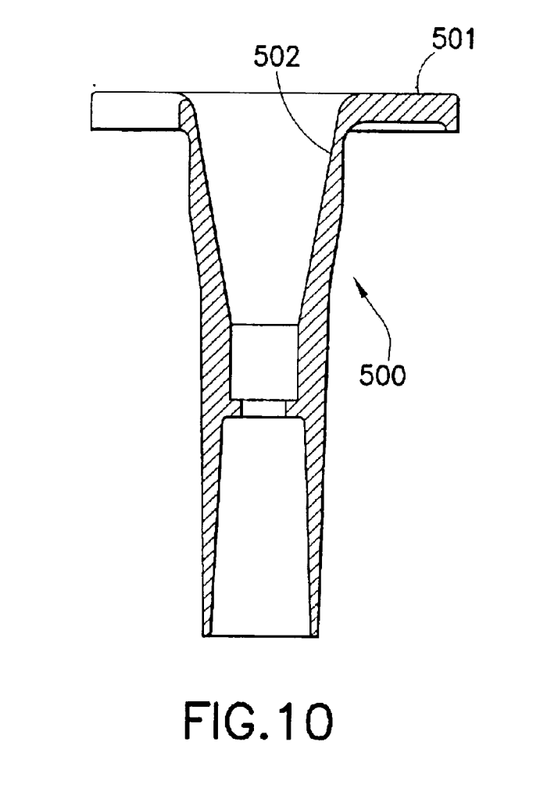
FIG. 10 is a cross-sectional view of the tibial component.

The control arm assembly 400, as shown in FIGS. 7–9, comprises a control arm 410, a post 420 and a conical bearing 430. The post 420 has medial and lateral side surfaces 421, an inferior recess 422, a post cam surface 423 and an anterior stop surface 424. The control arm 410 comprises a post support pin 412, a dovetail guide 413, a conical bearing support 414, a control arm boss 415 with control arm stop surfaces 416 and a stop pin 417.

The post 420 and conical bearing 403 preferably are formed from plastic and are assembled to the control arm 410 by pressing them on the post support pin 412 and conical bearing support 414 respectively. During assembly the inferior recess 422 of the post 420 engages the boss sidewalls 417 of the control arm 410 to prevent rotation of the post 420 on the post support pin 412. The tibial platform 500 has a superior bearing surface 501 and contains a conical hole 502 into which the conical bearing 403 of the control arm assembly 400 is placed on implantation. The tibial platform 500 can be the same as that described in U.S. Pat. No. 5,702,466. The embodiment shown here is a version used where an extension is added to the distal end of the platform to enhance fixation where needed.

The femoral component 200, the control arm 410 and tibial platform 500 preferably are made of titanium alloy coated with UltraCoat® TiN coating as disclosed in U.S. Pat. No. 5,702,448. However, these components can also be made of Co—Cr alloy. The bearing 300, post 420 and conical bearing 403 preferably are made of UHMWPe.

Figure 11:
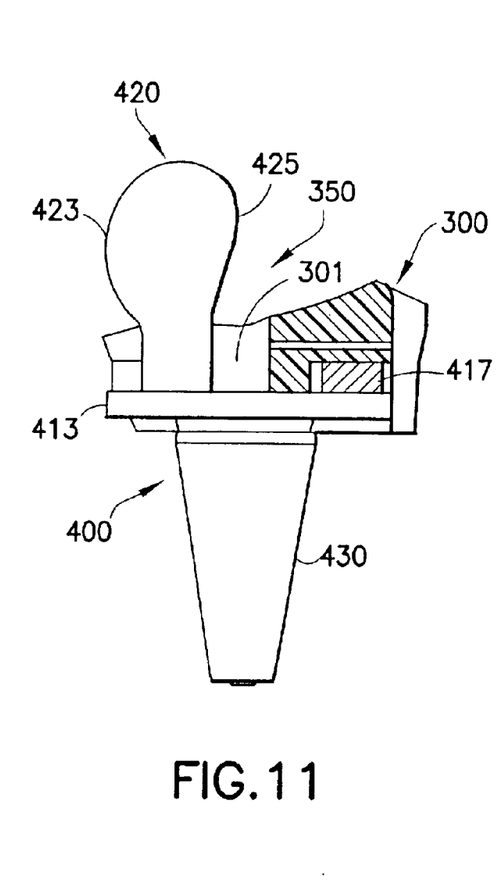
FIG. 11 is a side elevational view, partly in section, showing the subassembly of the bearing and control arm.
Figures 12, 13:
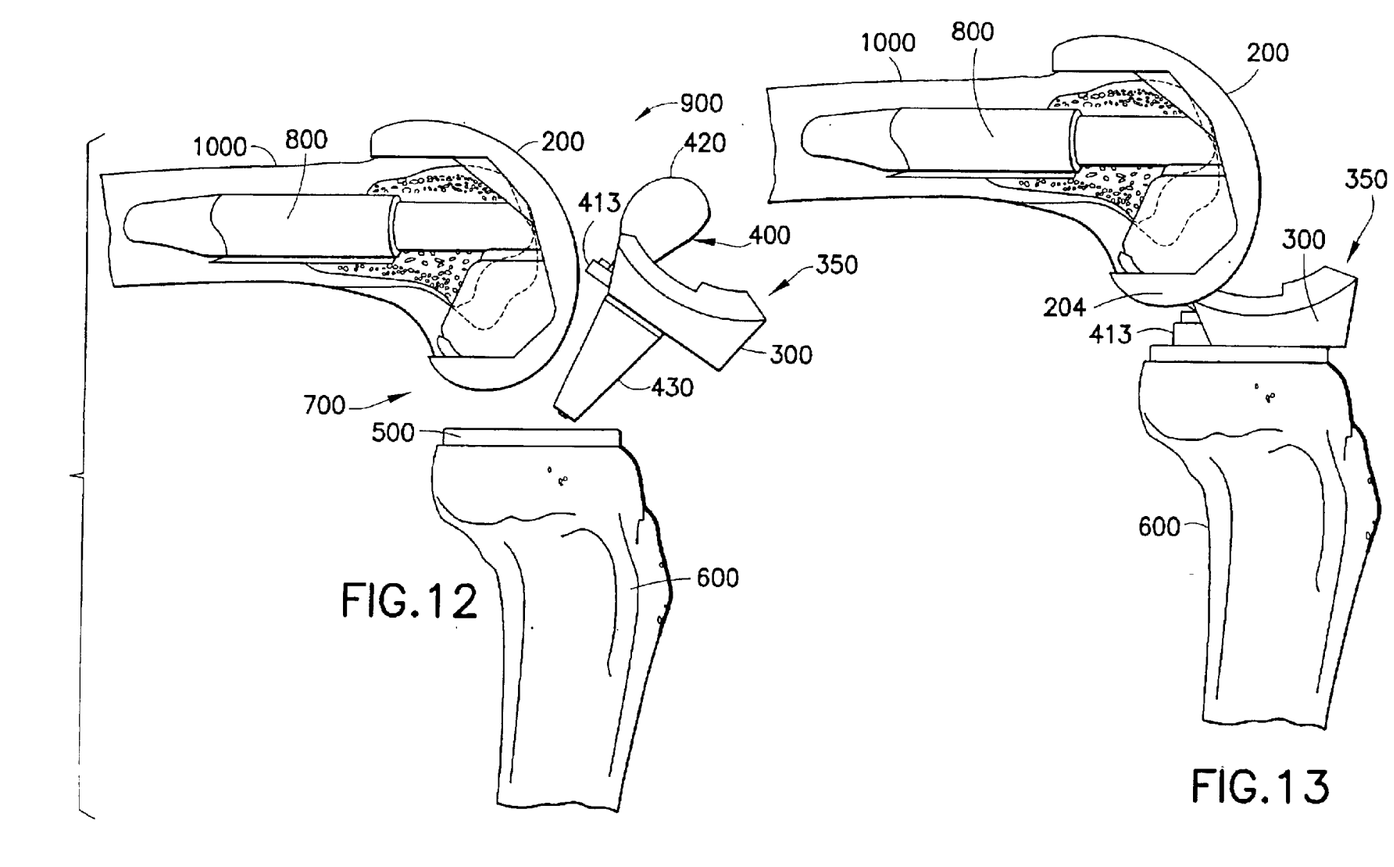
FIG. 12 is an exploded side elevational view showing implantation of the bearing.
FIG. 13 is a side elevational view similar to FIG. 12, but showing a later stage of implantation.
Figure 14:
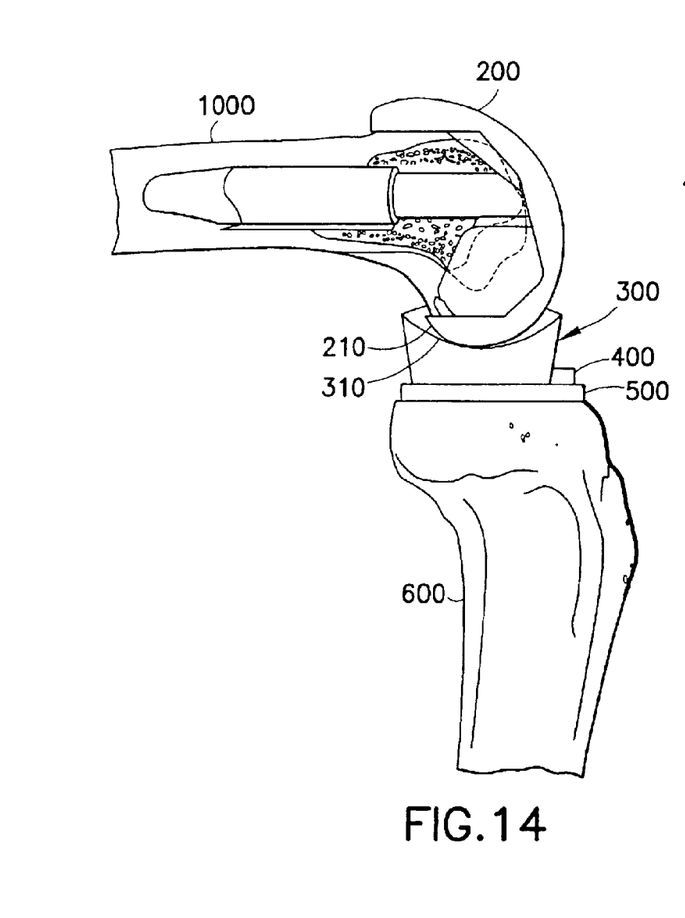
FIG. 14 is a side elevational view similar to FIGS. 12 and 13, but showing complete implantation.
Figure 15:
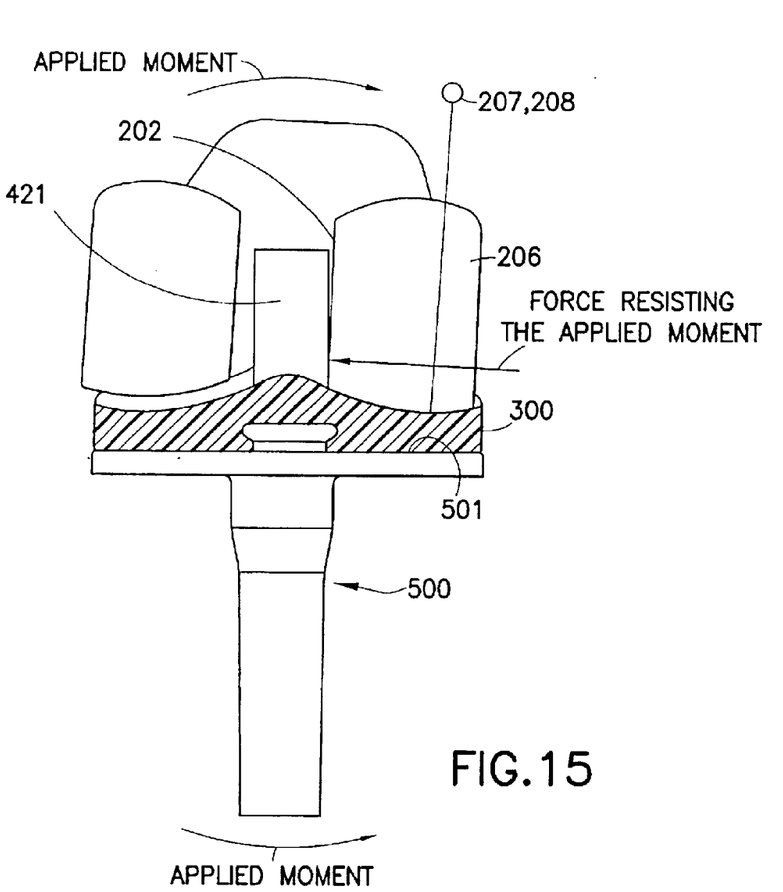
FIG. 15 is a rear elevational view of the assembled prosthetic component schematically showing forces applied thereto.

Implantation is illustrated in FIGS. 11–14. The tibial platform 500 is implanted into the tibia 600 and the femoral component assembly 900 consisting of the femoral component 200 with an attached extension 800 is inserted onto the femur 1000 in the usual fashion. The dovetail guide slot 302 of bearing 300 is engaged with the dovetail guide 413 of the control arm assembly 400 to produce a subassembly 350 as shown in FIG. 11. The subassembly 350 then is assembled onto the tibial platform 500 as shown in FIGS. 12 and 13 with the knee 700 flexed to about 100°. The bearing 300 then is pressed digitally in a posterior direction until the bearing 300 is seated under the femoral component as shown in FIGS. 13 and 14.

There are two means of valgus-varus stability. Under load bearing conditions the normal compressive load will press the femoral condyles 206 against the matching articular bearing surfaces 310. The match is such that under compression any rotation of the femoral component 200, in the plane of FIG. 13 must occur around an axis 207 through the center of curvature 208 of the femoral condyle 206. Rotation about axis 207 produces impingement between the medial and lateral surfaces 421 and box sidewalls 202. This contact produces a reaction force that resists any valgus-varus moment applied to the joint. Thus, bending of the post 420 and post support pin 412 need not occur to resist the applied moment. The outer medial and lateral side surfaces 421 may be made to slope outward distal so as to increase contact area with cam box 201.

During non-load bearing phases where any valgus-varus moment is quite small, the post may be subject to small bending loads since joint compression may not occur. The post support pin 412 must be strong enough in bending to resist such moments.

The cooperative action of the cam box 201 and post cam surface 423 are illustrated in FIGS. 16–21. These figures show the outer posterior condyle 206 of the femoral component 200 broken away and the bearing in cross-section so as to show the action of the cam surfaces and the posterior bearing stop means. In full extension, as shown in FIG. 16, the cam box surface 204 and post cam surface 423 need not be in contact. At such flexion angles they do not act to prevent anterior-posterior dislocation in the absence of load bearing. Under load bearing the shape of the femoral articular surface 210 pressing against the tibial articular surface 310 provides stability and position.

As flexion progresses, as shown in FIGS. 17–21, the anterior wall 211 of the box cam 201 of the femoral component 200 moves away from the post 420 of the control arm assembly 400. This allows play or translation, as limited by various surfaces of the cam box 201 and post 420, the stop pin 417 and stop recess 303 or the stop surfaces 304 and 416. The femoral cam surface 204 will engage the post cam surface 423 at about 45°. At flexion below 45° the post cam surface 423 plays no role in providing roll back. Roll back up to about 7.5 mm nevertheless can occur at such low flexion with the subject invention. This roll back can be generated by the action of tension in the patella tendon, which tends to pull the tibia anteriorly. The 7.5 mm play allowed is relatively normal and certainly less than the play that is present in most current prosthetic knee designs. Translation motion of the bearing 300 is limited to about 7.5 mm and roll back after about 120° of flexion produces some acceptable amount of climb so as to limit excess posterior motion of the bearing 300, which might otherwise produce impingement with posterior structures of the knee, thereby inhibiting flexion.

Figure 21:
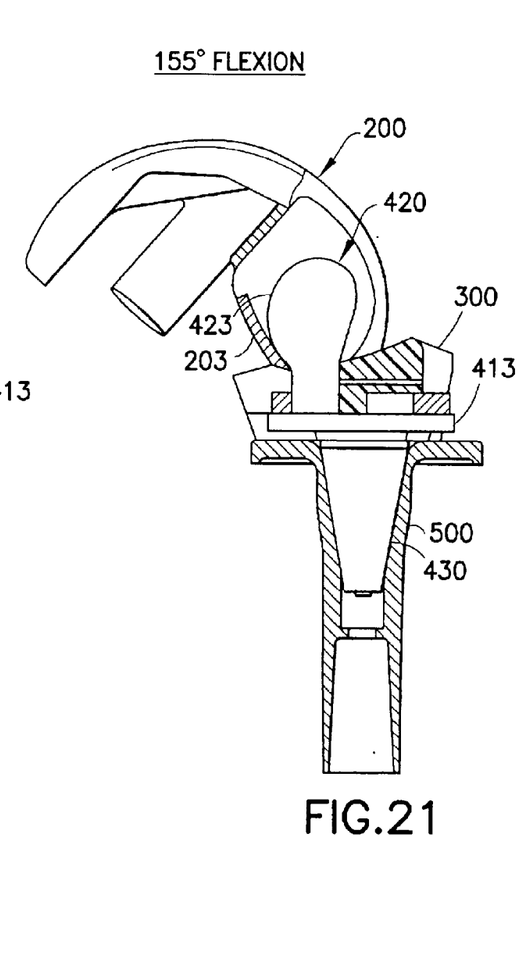
FIG. 21 is a cross-sectional view similar to FIGS. 16–20, but showing approximately 155°.
Figure 22:
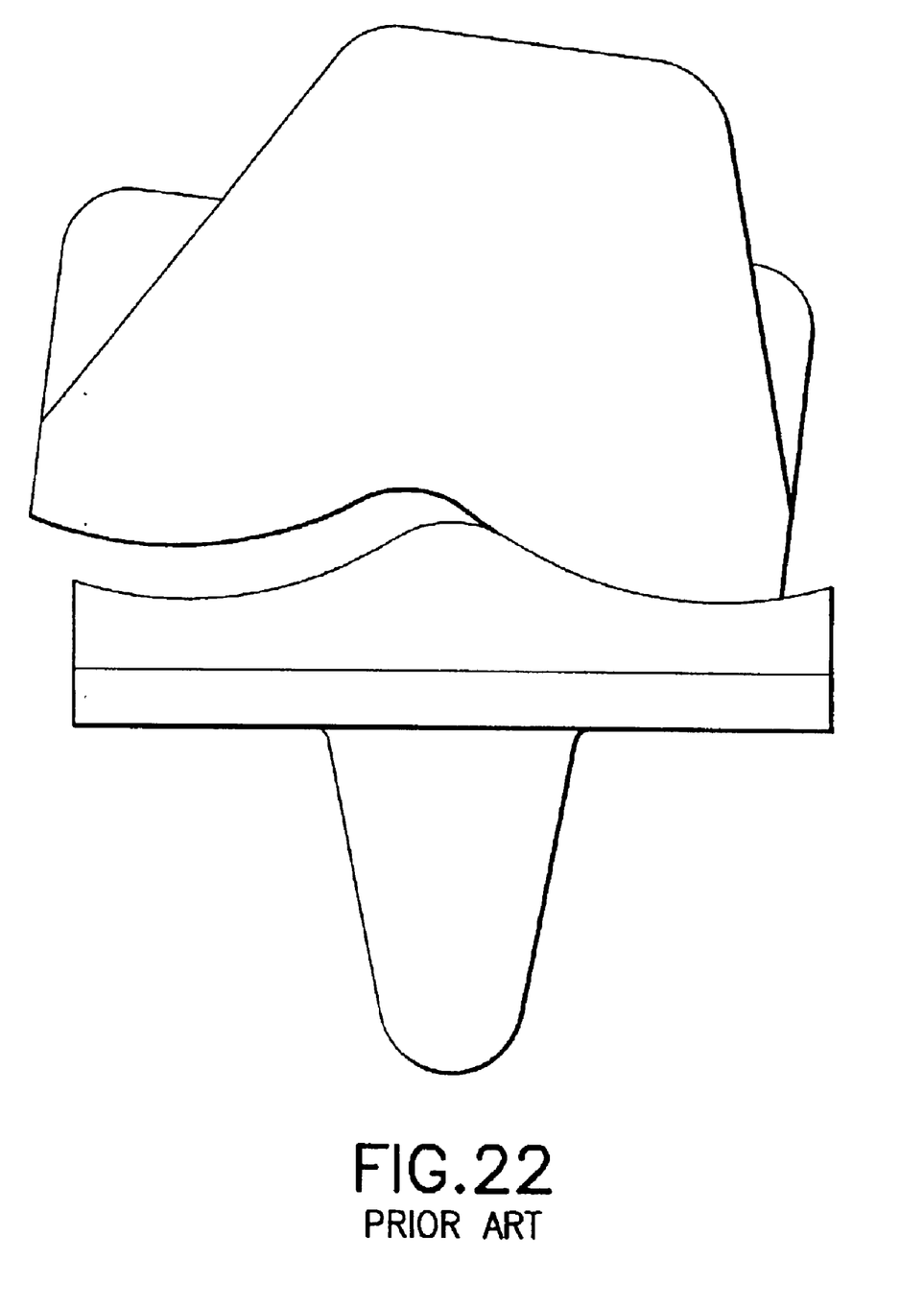
FIG. 22 is a rear elevational view of a prior art prosthesis showing dislocation

FIGS. 17–21 show that at the full illustrated range of flexion angles, the contact between the femoral cam 203 and the post cam surface 423 is always concave-to-convex, thus allowing for moderate contact stress. This differs from convex-to-convex or convex-to-planar contact which would produce substantially higher contact stresses. FIG. 21 shows that the illustrated embodiment enables 155° of flexion. This value is significantly greater then needed for most Western peoples, and is sufficient for deflection preferred by Asian people where sitting style may require high degrees of flexion.

Figure 23:
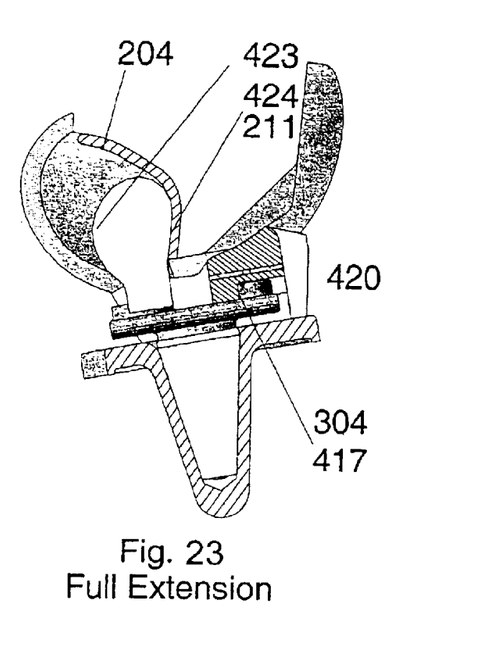
FIG. 23 is a cross-sectional view of an alternate prosthetic joint at full extension.

The cooperative action of the box cam 201 and post cam surface 423 for an alternate embodiment are illustrated in FIGS. 23–31. In full extension, as shown in FIG. 23, the box cam surface 204 and post cam surface 423 need not be in contact. At such flexion angles they do not act to prevent anterior-posterior dislocation in the absence of load bearing, as is the case in the first embodiment. Under load bearing the shape of the femoral articular surface 210 pressing against the tibial articular surface 310 provides stability and position as shown in FIG. 23.

Full extension in the normal knee also produces anterior-posterior stability due to the tightening action of the cruciate ligaments at full extension. Thus this design produces normal full extension stability against translation. As shown in FIG. 23 there is no anterior-posterior slop in full extension since the femoral component and bearing are trapped between the contact of post face 424 and wall 211 and the contact of stop pin 417 and bearing stop surface 304.

Figure 24:
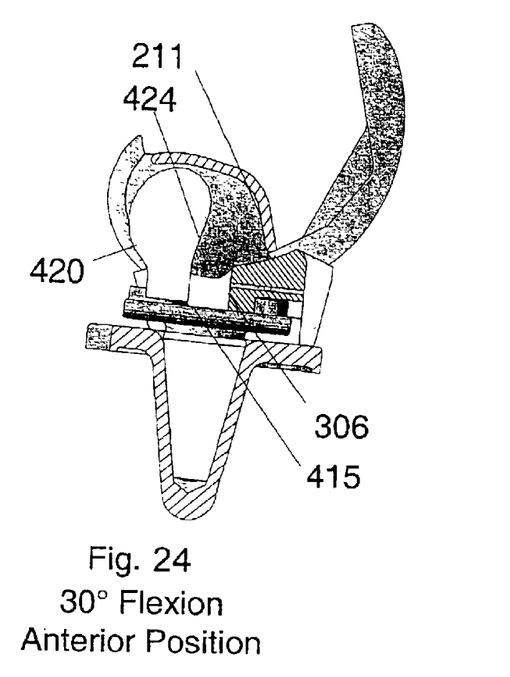
FIG. 24 is a cross-sectional view similar to FIG. 23, but showing a 30° flexion—anterior position.

As flexion progresses, as shown in FIG. 24, wall 211 moves away from the post 420.

This allows "slop" or translation as limited by various surfaces of the cam box 201 and post 420, or stop pin 417 and bearing stop surface 304 or stop surfaces 415 and 306.

At flexion below 35° the post cam surface 423 plays no role in providing rollback.

Figure 25:
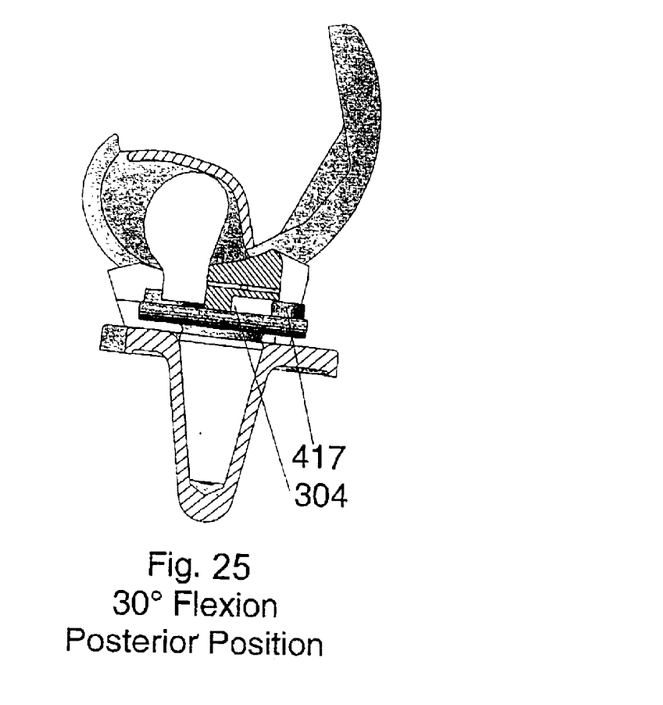
FIG. 25 is a cross-sectional view similar to FIGS. 23 and 24, but showing a 30° flexion—posterior position.

Rollback up to about 7.5 mm can still, however, occur at such low flexion with the disclosed embodiment as is shown in FIG. 25. (All distances given are for the size 3 (standard) size knee. Other size distances are proportional.) This rollback can be generated by the action of the tension in the patella tendon, which tends to pull the tibia anteriorly when it is acting. The 7.5 mm of play allowed is only moderately in excess of normal (0–5 mm) and certainly less than that present in most current knee designs. Translation motion of the bearing is limited to about 7.5 mm and rollback after about 75° of flexion produces some small, admissible amount of climb so as to limit excess posterior motion of the bearing. This excess posterior motion could increase impingement with posterior structures of the knee inhibiting flexion.

Figure 26:
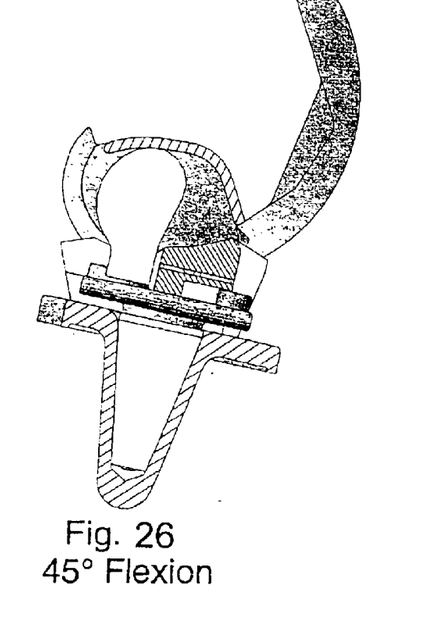
FIG. 26 is a cross-sectional view similar to FIGS. 23–25, but showing approximately 45° flexion.
Figure 27:
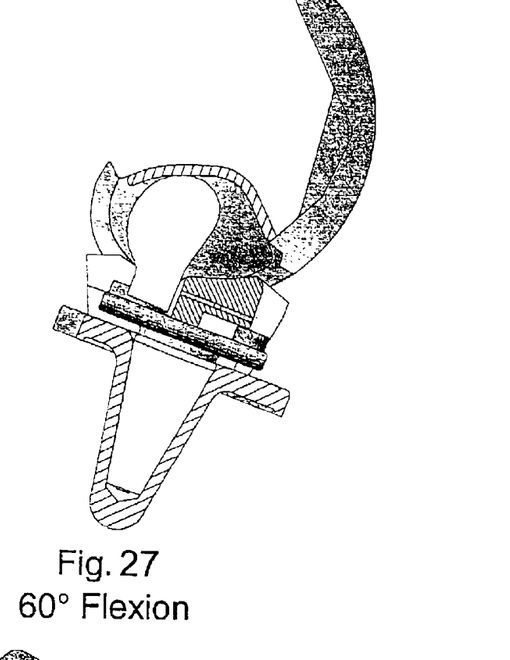
FIG. 27 is a cross-sectional view similar to FIGS. 23–26, but showing approximately 60° flexion.

As flexion progresses further, as shown in FIGS. 26–31, the box cam surface 204 will engage the post cam surface 423 at about 35° if the femur has not moved posteriorly as the result of muscle, or other, forces. Flexion beyond 35° will then force the femoral component 200 posteriorly as shown in FIG. 26. The compressive force on the bearing and its concave shape of its articulating surface will cause the bearing 300 to move posteriorly with the contact point between femoral component 200 and the bearing 300. This posterior movement, or femoral rollback, improves quadriceps effectiveness as is well known. This rollback is present for normal load bearing activity likely to be performed by a knee replacement patient requiring a posterior stabilizer device. At 45° to 60° rollback is about 6.5 mm, at 90° rollback is about 9.5 mm and at 120° about 10.5 mm. At the maximum flexion of 162° rollback is also maximum and is about 13 mm.

Figure 28:
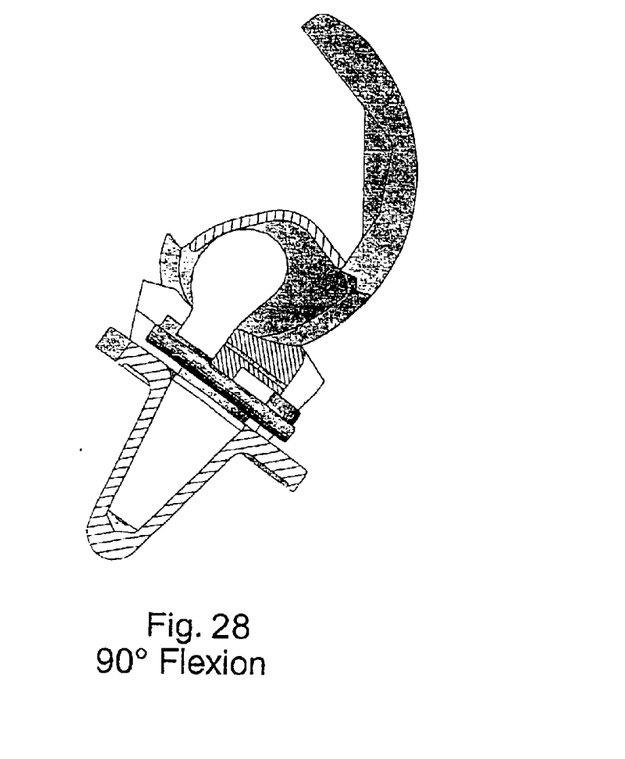
FIG. 28 is a cross-sectional view similar to FIGS. 23–27, but showing approximately 90° flexion.
Figure 29:
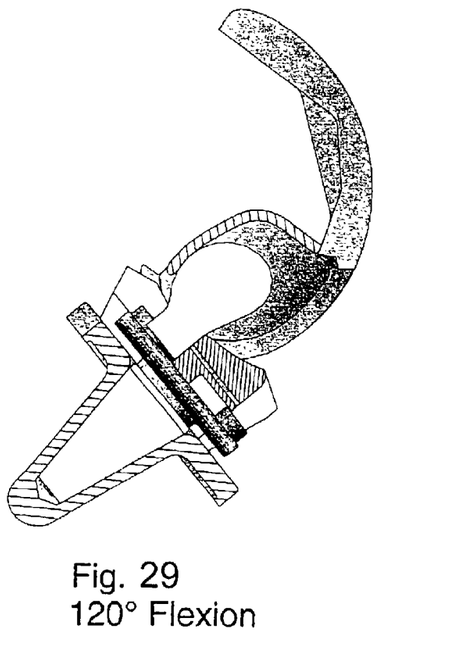
FIG. 29 is a cross-sectional view similar to FIGS. 23–28, but showing approximately 120° flexion.
Figure 30:
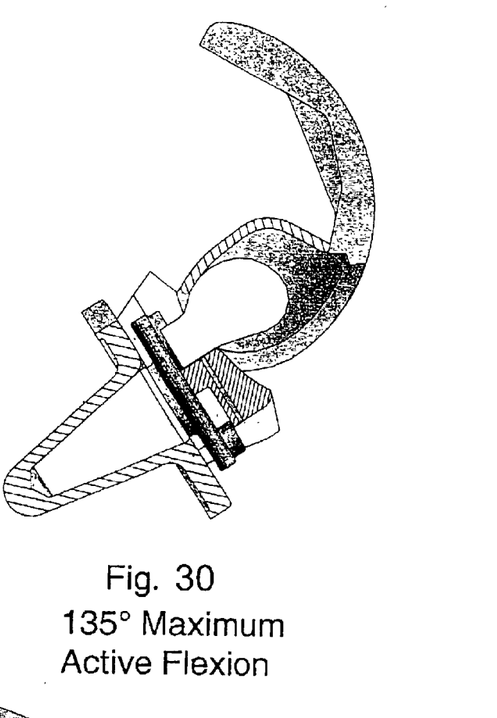
FIG. 30 is a cross-sectional view similar to FIGS. 23–29, but showing approximately 135°, maximum active flexion.
Figure 31:
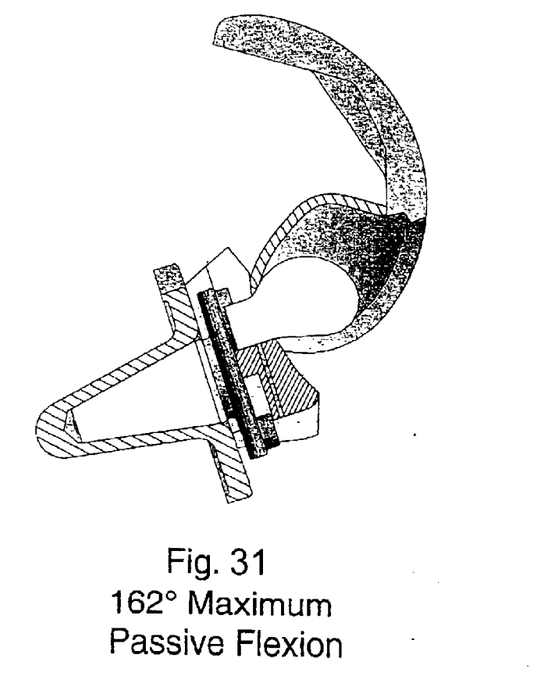
FIG. 31 is a cross-sectional view similar to FIGS. 23–30 but showing approximately 162°, maximum passive flexion.

Slightly beyond 75° of flexion it may be desirable to prevent additional posterior motion of the bearing to prevent this motion from being excessive. Avoiding this excessive motion avoids the slop associated with it and also reduces impingement between the posterior aspect 305 of the bearing and posterior tissues, which may inhibit flexion. This is accomplished in this embodiment by having stop surface 415 engage posterior stop surface 306 as shown in FIG. 28. Additional rollback would then be accompanied by some "climb" of the femoral component over the articular surface of the bearing. In the embodiment here this effect is small. At 90° of flexion there is about 2 mm posterior translation of the femur on the bearing surface. This produces an additional shearing force of about 16% of body weight ignoring the effects of friction that tends to reduce this added force. At 120° of flexion, rollback on the bearing is about 3 mm and produces an additional shearing force of about 24%. This latter rollback represents a lift of only about 0.12 mm. Such flexion is infrequently encountered and the force increase is moderate. At the maximum of 162° of flexion climb on the bearing is about 5 mm with a small lift of 0.4 mm. Such flexion is, however, passive and thus there is no significant loading associated with it.

The embodiment of FIGS. 23–31 has several other advantageous features. In particular, as flexion progresses a gradual clearance develops which allows about 7.5 mm of rollback. Thus rollback approaching normal is available at 30° of flexion. At 35° the femoral cam 203 engages the post cam surface 423 and begins the development of forced rollback. Thus significant rollback starts much earlier than the 70° typical of the earlier designs. Additionally, for all load bearing flexion angles the contact between femoral cam 203 and post cam surface 423 is always concave to convex thus allowing for moderate contact stresses in a contact where contact stresses in earlier designs are always excessive. The height of the post is significantly greater improving posterior dislocation resistance. Although conventional posterior stabilizer devices reduce such dislocation they do not eliminate it. The embodiment disclosed herein is superior in its posterior dislocation resistance due to this increased height as well as the action of the femoral box wall 211. This wall also resists anterior dislocation at low and moderate flexion angles. This embodiment allows 162° of flexion a value significantly greater than needed for use by western peoples and sufficient for Asiatic peoples.

Additionally rollback at moderate flexion angles, where the most frequent activities occur, does not produce any significant "climb" in the disclosed prosthetic device. At such flexion angles, rollback approaching normal is available without any significant increase in shearing forces associated with such climb. Rollback is significantly greater at very deep flexion than in moderate flexion. Here climb does occur to some degree, but the increase in shear loading is moderate for active flexion. Rollback is greatest at angles associated with passive flexion where the knee is not load bearing. This additional rollback is important in obtaining greater flexion by increasing anterior movement of the tibia relative to the femur reducing posterior tissue impingement restricting flexion.

What is claimed is:

1. A knee joint prosthesis comprising:
a femoral component having a superior surface for mounting to a femur, an inferior articular bearing surface with medial and lateral convex condyles, a cam box extending between the superior and inferior surfaces in a posterior portion of said femoral component, said cam box comprising medial and lateral walls and a cam wall extending between said medial and lateral walls, said cam wall having an inferior continuously concave femoral cam surface;
a tibial component;
a bearing disposed between the femoral and tibial components, the bearing having a concave superior bearing face in articular bearing engagement with the convex condyles of the femoral component, the concave superior bearing face being configured for non-congruent bearing engagement with the convex condyles during selected ranges of flexion of the knee joint prosthesis, the bearing further having an inferior bearing face in sliding and rotational bearing engagement with the tibial component, a notch extending anteriorly into a posterior face of the bearing and a groove formed in the inferior bearing face of the bearing and extending anteriorly from the notch; and
a control arm assembly comprising a control arm slidably engaged in the groove of the bearing for permitting movement of the bearing along the control arm, pivotal connection means extending from the control arm for permitting pivotal movement of the control arm relative to the tibial component and a post extending superiorly from the control arm, the post being slidably engaged in the notch of the bearing and disposed in the cam box of the femoral component, the post having a convex cam surface disposed for engaging the concave femoral cam surface through a range of flexion from approximately 35° to at least 155° for generating roll back of the femoral component on the bearing during flexion of the knee joint.

2. The knee joint prosthesis of claim 1, wherein the convex cam surface of the post engages the concave femoral cam surface continuously to approximately 162° of flexion.

3. The knee joint prosthesis of claim 1, wherein the cam surface of the post is a compound curve comprising a plurality of sequentially contiguous arc sections generated about parallel axes.

4. The knee joint prosthesis of claim 1, wherein the post has medial and lateral surfaces slidably engaging the medial and lateral walls of the cam box for resisting valgus-varus moments.

5. The knee joint prosthesis of claim 4, wherein the control arm of the control arm assembly is formed from a metal material and wherein the post of the control arm assembly is formed from plastic.

6. The knee joint prosthesis of claim 5, wherein the control arm of the control arm assembly comprises a metallic post support pin, the plastic post being non-rotatably mounted on the metallic post support pin.

7. The knee joint prosthesis of claim 6, wherein the pivotal connection means of the control arm assembly comprises a conically generated bearing formed from a plastic material.

8. The knee joint prosthesis of claim 7, wherein the control arm of the control arm assembly includes a metallic conical bearing support, said conical bearing being mounted to the conical bearing support.

* * * * *